United States Patent
Moazed

[11] Patent Number: 5,993,407
[45] Date of Patent: Nov. 30, 1999

[54] TRANSNASAL LACRIMAL INSERT

[76] Inventor: Kambiz Thomas Moazed, 106 E. 85th St. #1F, New York, N.Y. 10028

[21] Appl. No.: 08/736,902

[22] Filed: Oct. 25, 1996

[51] Int. Cl.[6] .................................................. A61M 5/00
[52] U.S. Cl. ................................................... 604/8
[58] Field of Search .................................... 604/8, 9, 10

[56] References Cited

U.S. PATENT DOCUMENTS

| | | | |
|---|---|---|---|
| 4,886,488 | 12/1989 | White | 604/9 |
| 4,915,684 | 4/1990 | MacKeen et al. | 604/8 |
| 5,318,513 | 6/1994 | Leib et al. | 604/8 |
| 5,334,137 | 8/1994 | Freeman | 604/8 |
| 5,346,464 | 9/1994 | Camras | 604/8 |
| 5,417,651 | 5/1995 | Guena et al. | 604/8 |
| 5,437,625 | 8/1995 | Kurihashi | 604/8 |

OTHER PUBLICATIONS

Moazed, K. et al., "Dacryocystorhinostomy," *Surgery of the Paranasal Sinuses*, Chapter 14, pp. 224–239. 1985.

*Primary Examiner*—Ronald K. Stright, Jr.
*Assistant Examiner*—Patricia M. Bianco
*Attorney, Agent, or Firm*—Kenyon & Kenyon

[57] ABSTRACT

A temporary transnasal lacrimal insert is used in a surgical procedure for improving drainage from a patient's lacrimal sac to his or her nasal cavity. The insert includes a tubular member with a proximal end and an enlarged distal end. The insert also includes an attachment element about which ends of a tube can be fastened. In the procedure, a hole is created extending from the lacrimal sac into the nasal cavity using surgical techniques or a laser probe. Then, opposite ends of a tube are introduced through the patient's upper and lower puncta, through the patient's upper and lower canaliculi, through the lacrimal sac, through the hole, and into the nasal cavity. The ends of the tube are then threaded through the passage in the insert. The insert is then placed from the nasal cavity into the hole by forcing the proximal end of the insert through the hole and into the lacrimal sac, and abutting the enlarged distal end, which is larger than the hole, against a surface in the nasal cavity surrounding the hole. The ends of the tube are then fastened to the attachment element of the insert. Excess tube extending into the nasal cavity is then cut short to reduce nasal irritation. After the hole has sufficiently healed in about 3–6 months, the tube and the insert are removed.

1 Claim, 4 Drawing Sheets

TRANSNASAL LACRIMAL INSERT

FIELD OF THE INVENTION

The present invention relates generally to medical devices and procedures and, more particularly, to devices and procedures for lacrimal tract surgery for improving tear drainage.

BACKGROUND OF THE INVENTION

One of the major problems with known dacryocystorhinostomy (DCR) procedures for improving lacrimal tract drainage is closure of the induced drainage hole between the lacrimal sac and the nasal cavity. The possibility of hole closure exists even with the newer improved laser DCR techniques.

In procedures for improving drainage using nasolacrimal tubes or stents, the tubes are inserted from the conjunctiva or the lacrimal sac into the nasal cavity. Common problems with these devices include disinsertion, protrusion and dislocation of and intolerance to the tubes.

Accordingly, one object of the present invention is to provide an insert usable in a procedure for providing lacrimal tract drainage that is stable, temporary, and that preserves the draining function of the nasolacrimal duct after surgery. Another object of the invention is to provide a device that keeps the rhinostomy hole open during the healing process after surgery. A further object of the invention is to provide an insert that is easily inserted and is easily accessible and removable after its task has been accomplished. Another object of the invention is to provide an insert that stabilizes and substantially prevents dislocation of a silastic tube installed in the lacrimal tract.

SUMMARY OF THE INVENTION

In accordance with the present invention, a transnasal lacrimal insert is provided for use in a surgical procedure for improving drainage from a patient's lacrimal sac to his or her nasal cavity. The insert includes a tubular member having a proximal end and an enlarged distal end. The insert also includes a rod about which ends of a flexible tube can be fastened.

In the procedure, a hole is created extending from the lacrimal sac into the nasal cavity using surgical techniques or a laser probe. Then, opposite ends of a tube are introduced through the patient's upper and lower puncta, through the patient's upper and lower canaliculi, through the lacrimal sac, through the hole, and through the nasal cavity. The ends of the tube are then threaded through the passage in the insert. The insert is then inserted through the nasal cavity into the hole by forcing the proximal end of the insert through the hole and into the lacrimal sac, and abutting the enlarged distal end, which is larger than the hole, against a surface in the nasal cavity surrounding the hole. The ends of the tube are then fastened to the rod in the insert. Excess tube extending from the nasal cavity is then cut short. After the hole has sufficiently healed in about 3–6 months, the tube and the insert are removed.

DETAILED DESCRIPTION

Figure 1:
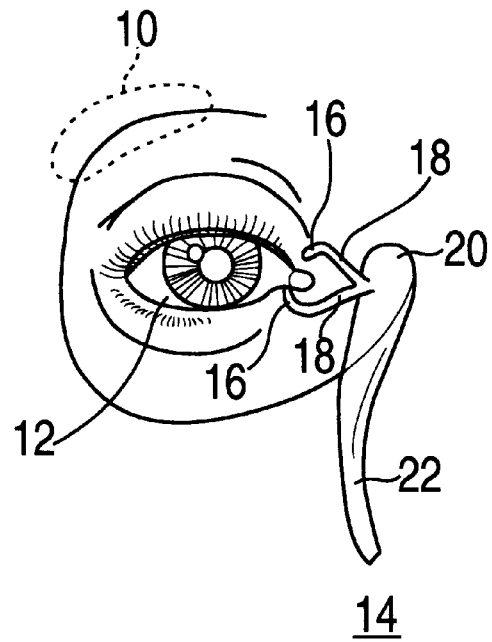
FIG. 1 is a front, part-sectioned view of the human lacrimal tract.

FIG. 1 illustrates the anatomy of the human lacrimal tract. Secretory or lacrimal glands 10 above the eye 12 produce tears, which cover the anterior surface of the eye 12. A lacrimal excretory system or tear drainage system is provided for draining tears into the nasal cavity 14. The lacrimal excretory system includes upper and lower puncta (or openings) 16 at the upper and lower eyelids, respectively, and upper and lower canaliculi 18 leading from the corresponding puncta 16 into a lacrimal sac 20. A nasolacrimal duct 22 connects the lacrimal sac 20 to the nasal cavity 14.

Obstruction or closure of the drainage system at the nasolacrimal duct 22 can cause constant tearing, recurrent infection of the lacrimal sac (Dacryocystitis), and spread of infection to the adjacent tissues (Orbital cellulitis) and to the brain (Brain abscess).

Common causes of nasolacrimal duct obstruction include congenital occlusion in children, idiopathy, trauma, chronic infections, tumors, foreign bodies, and heredity.

There are several known methods of treating nasolacrimal obstruction. For instance, nasolacrimal obstruction in children can be treated by probing the nasolactrimal duct. However, this procedure is only feasible for use in children.

In another procedure known as Conjunctivodacryocystorhinostomy, the lacrimal excretory system is completely bypassed. In this procedure, a passage from the eye to the nose is opened by surgery and a tube (typically a Jones tube or a Cooper tube) is installed in the passage to completely bypass the lacrimal excretory system.

In DCR procedures, a passage from the lacrimal sac to the nose is opened by surgery with or without installing a tube.

A number of problems are associated with these known procedures. First, they are generally major surgical procedures that are difficult and time consuming. Also, most of the procedures require general anesthesia. In addition, most of the procedures require facial incision and are typically very bloody. Patients are also likely to feel substantial pain and discomfort in the post-operative period.

The tubes used in procedures involving tube installation are permanent and large. They can become clogged after installation by mucus or secretions. In addition, in many cases, bacterial colonization at the tubes will produce odor. Also, dislocation and protrusion of tubes is not uncommon.

Figure 2:
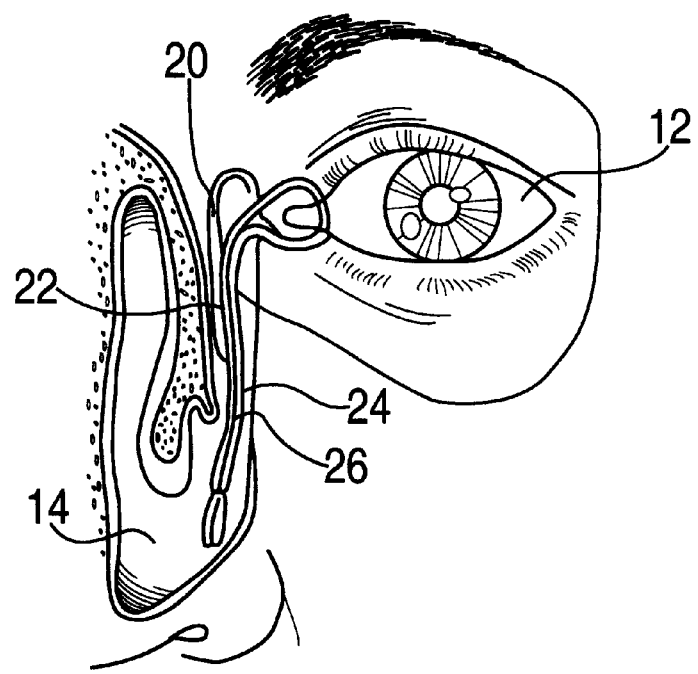
FIG. 2 is a front, part-sectioned view of the lacrimal tract illustrating use of a tube in accordance with a prior art laser DCR procedure.

The newer laser DCR procedure is a significant improvement over the other known procedures. In the laser DCR procedure, a passage from the lacrimal sac to the nose is opened by a laser probe followed by intubation as shown in FIG. 2.

Unlike the other procedures, laser DCR is a minor surgical procedure and is performed under local anesthesia. It is also relatively easy to perform, and it takes only about 10–15 minutes. No facial incision is involved, and there is substantially no blood loss. Also, there is minimal post-operative pain. Furthermore, no permanent tubes are used in the procedure.

In the laser DCR procedure, the lacrimal sac 20 is first inflated with Healon, a clear viscous liquid. A fiber optic laser probe (not shown) is then passed into the puncta 16, through a canaliculus 18 and into the sac 20. The tip of an endoscope (not shown) is placed in the nasal cavity 14 to confirm proper positioning of the probe. Laser energy is then applied by the probe to form a rhinostomy hole 24 having a diameter of about 5–7 mm extending from the lacrimal sac 20 into the nasal cavity 14. Thereafter, the laser probe and endoscope are removed. Next, a tube 26 is installed. Metal tips (not shown) at opposite ends of the silastic tube 26 are passed from upper and lower puncta 16 into their respective canaliculi 18, into the sac 20 and then through the laser induced hole 24 into the nasal cavity 14. The ends of the tube 26 are then tied in a knot inside the nasal cavity, and excess tube including the metal tips are cut short as shown in FIG. 2. The tube 26 is removed after 3–6 months with the expectation that the laser induced hole 24 will remain open during the healing process.

There are, however, a number of problems associated with this procedure. First, the laser induced hole 24 tends to close due to its small diameter. Also, the knot can be easily displaced from nasal cavity 14 into the lacrimal sac 20 by, for example, nose blowing and sneezing. Dislocation of the silastic tube 26 often results in a spontaneous closing of the hole 24. In addition, the knot may cause nasal irritation due to its significant extension into the nasal cavity 14.

Figure 3:
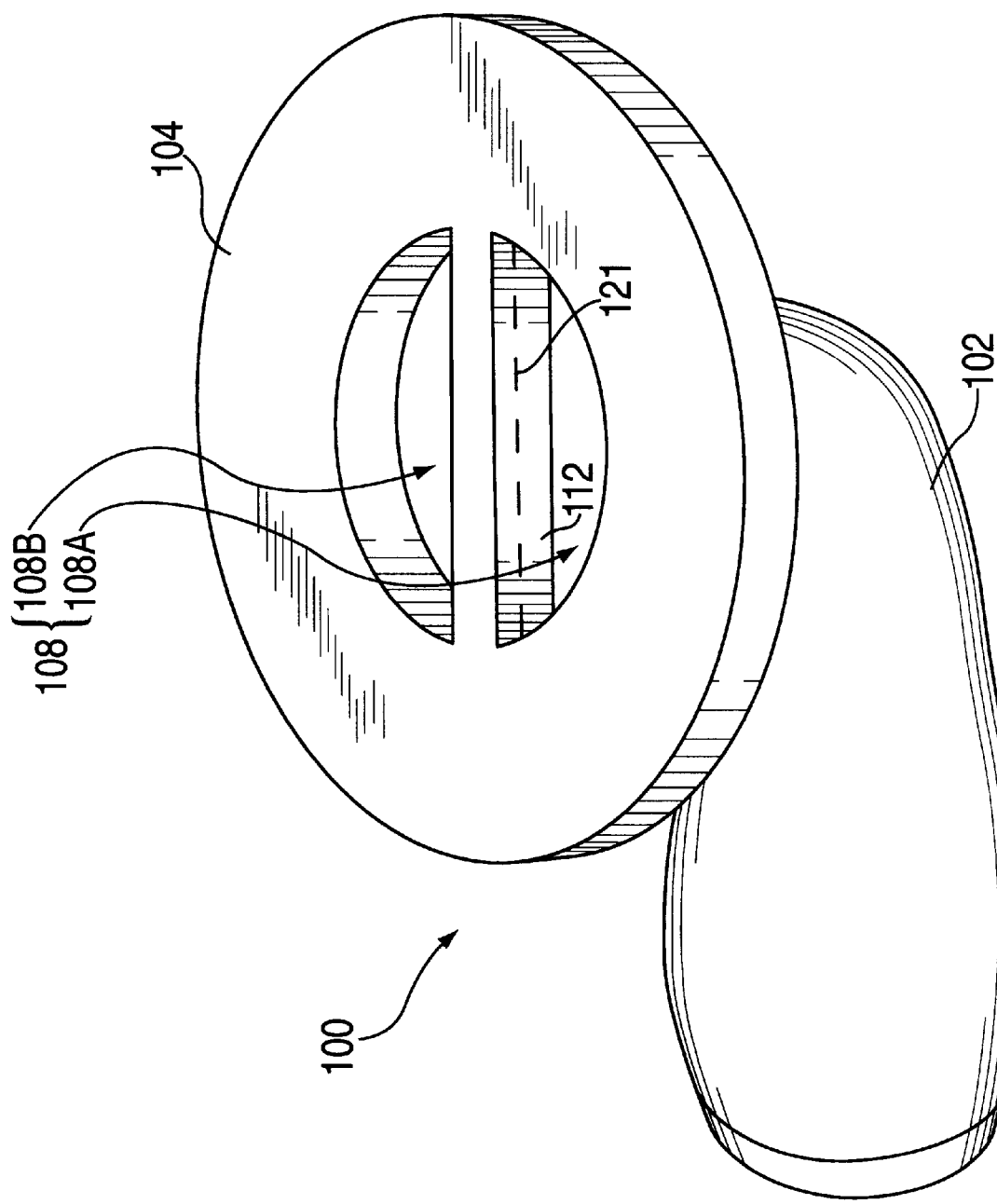
FIG. 3 is a perspective view of a transnasal lacrimal insert in accordance with the invention.
Figure 4:
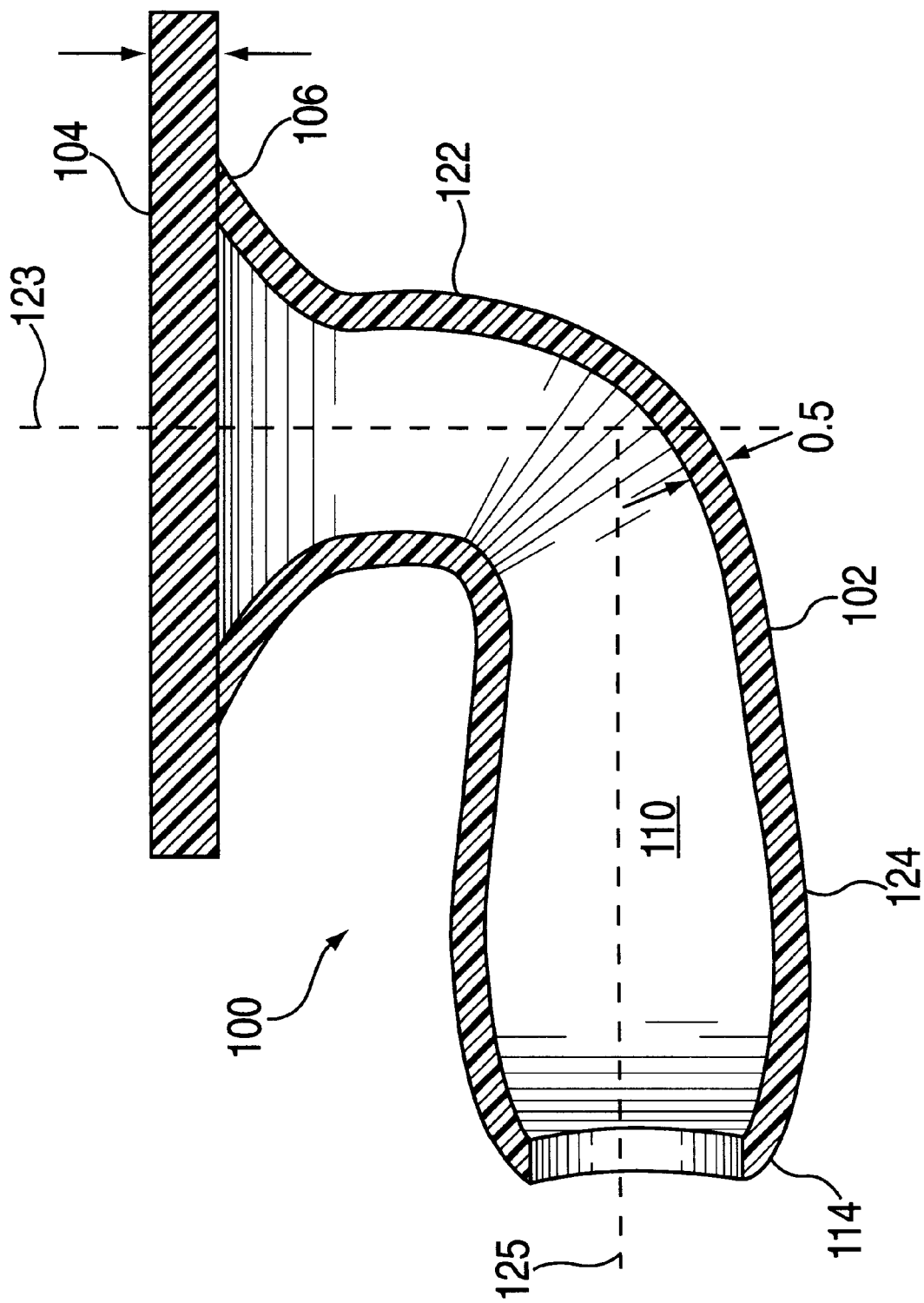
FIG. 4 is a side section view of the FIG. 3 insert.

In accordance with the present invention, a transnasal lacrimal insert 100 is provided for use in a procedure for providing lacrimal tract drainage. As shown in FIGS. 3 and 4, the insert 100 comprises a generally L-shaped tubular member 102 with a circular base 104 flanged at one end 106 (which will be referred to as the enlarged distal or nasal end 106) of the tubular member 102. The base 104 includes an opening 108 leading to the passage 110 extending through the tubular member 102. A rod 112 having a longitudinal axis 121, as shown in FIG. 3, is disposed within the opening 108 and extends across the opening 108 dividing the opening 108 into two semi-circular openings 108A and 108B. The rod forms an attachment element about which ends of a tube can be fastened as will be described in further detail below. The tubes may be comprised of a wide variety of flexible low-friction, biocompatible materials well known to those skilled in the art as suitable for this purpose, however, in an especially preferred embodiment the tubes are comprised of Silastic™ available from Dow Corning. The opposite end 114 of the tubular member 102, which will be referred to as the lacrimal or proximal end, is tapered forming a generally sharp edge to facilitate penetration of the insert 100 into a rhinostomy hole as will be further described below. As shown in FIG. 4, the L-shaped tubular member is comprised of a first portion 122 having a first axis 123 and a second portion 124 having a second axis 125. In an especially preferred embodiment, the first axis 123 and the second axis 125 are substantially perpendicular.

The insert 100 comprises a biocompatible material suitable for use in contact with tissue. It is preferably a soft, flexible material such as, for example, silicone and Silastic™ available from Dow Corning.

The tubular member 102 has a wall thickness of about 0.5 mm to 1 mm. The base 104 has a thickness of about 0.5 mm to 1 mm and an outer diameter of about 10 mm.

A variety of inserts having different tubular member lengths (indicated by the dimension "L" in FIG. 4) can be provided depending on the patient on which it is to be used. For example, inserts having tubular member lengths of 8 mm, 10 mm, 12 mm and 14 mm can be provided.

The initial steps of the procedure using the insert 100 in accordance with the invention are similar to those of the laser DCR procedure previously discussed. The lacrimal sac is first inflated with Healon. A fiber optic laser probe (not shown) is then passed into a puncta 16, through a canaliculus 18 and into the lacrimal sac 20. The tip of an endoscope (not shown) is placed in the nasal cavity 14 to confirm proper positioning of the probe. Laser energy is then applied by the probe to open a hole 116 from the lacrimal sac 20 into the nasal cavity 14. The probe is moved about and back and forth during this step to enlarge the hole to a diameter of about 5–7 mm. Thereafter, the laser probe and endoscope are removed.

Next, a tube 120 is installed. Metal tips at opposite ends of the tube are passed from upper and lower puncta 16, through the respective upper and lower canaliculi 18 into the sac 20, then through the laser induced hole 116, and through the nasal cavity 14 to outside the patient's nose.

Figure 5:
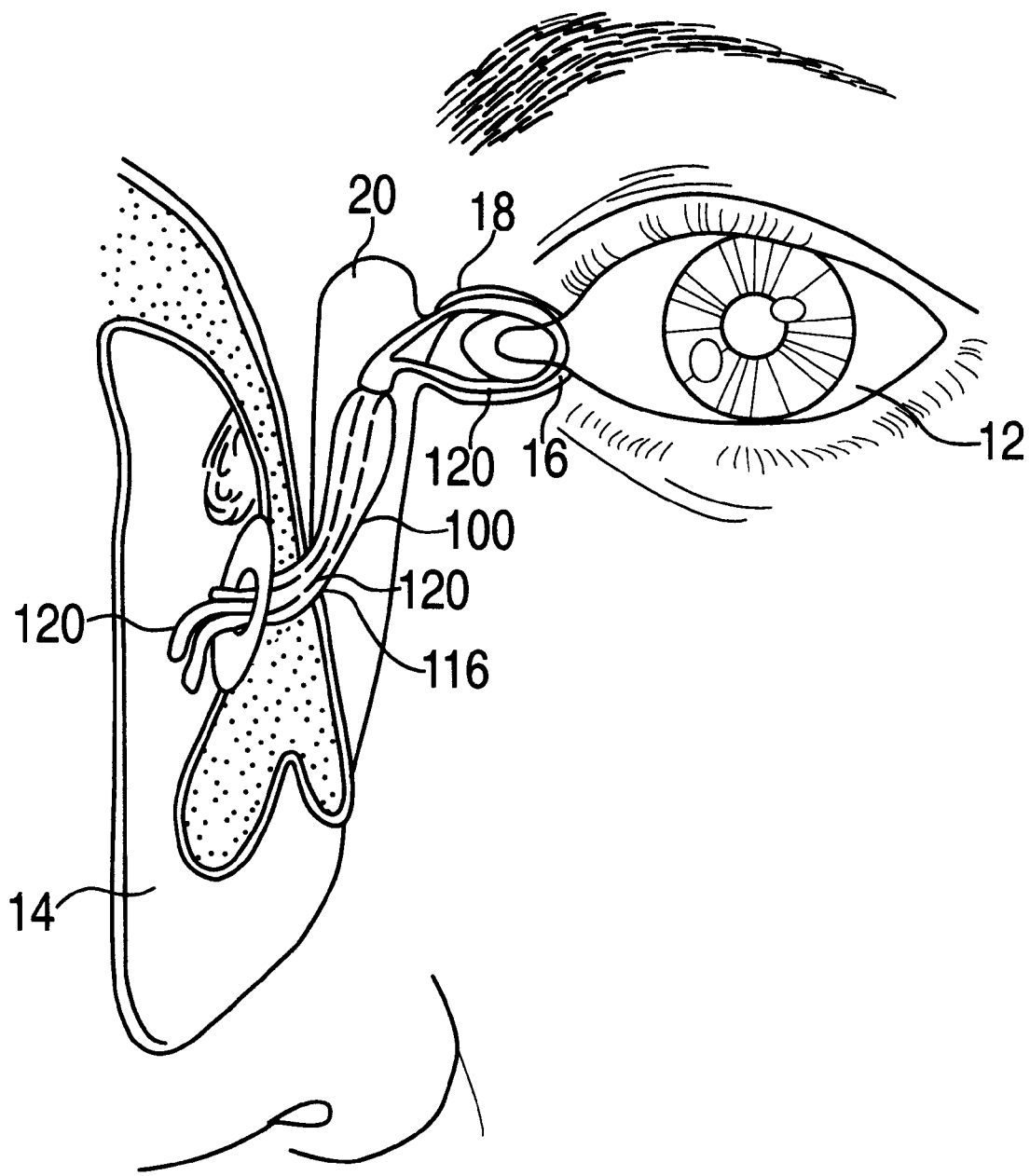
FIG. 5 is a front, part-sectioned view of the lacrimal tract illustrating use of the insert in accordance with the invention.

The metal ends of the silastic tube 120 are then threaded through the passage 110 in the insert 100. The tube ends are each introduced through the proximal end 114 of the insert 100 and out of a different one of the openings 108A and 108B in the base 104. The insert 100 is then introduced from the nasal cavity 14 into the laser induced hole 116 by forcing the tapered proximal end 114 of the insert 100 through the hole 116 and into the lacrimal sac 20. The base 104 will abut the surface of the nasal cavity 14 surrounding the hole 116 since the base 104 will have a larger diameter than the hole 116. The insert 100 will accordingly be kept from being displaced into the lacrimal sac 20. The ends of the tube 120 are then tied about the rod 112 at the base 104. Excess tube extending into the nasal cavity including the metal tips is then cut short as shown in FIG. 5.

The tube 120 keeps the insert 100 from falling out of the hole 116 into the nasal cavity 14. At the same time, the insert 100 keeps the silastic tube from being displaced into the lacrimal sac.

The tube 120 and the insert 100 are removed after about 3–6 months after the hole 116 has healed sufficiently.

This procedure has a number of significant advantages over the conventional laser DCR and other procedures previously described. First, the insert 100 substantially prevents hole closure by mechanical resistance. Migration of epithelium occurs around the insert 100 to reduce the likelihood of closure.

The insert 100 is also temporary, and it therefore does not have the problems associated with permanent tubes.

The presence of the insert 100 enables a significantly shorter tube extension into the nasal cavity, thereby reducing nasal irritation.

By tying the knot of the silastic tube to the rod of the insert 100, the knot is kept from dislocating into the lacrimal sac.

In addition, protrusion and loop formation of the tube is prevented at the medial canthus.

Also, the insert 100 permits drainage to be preserved immediately after surgery.

Furthermore, the insert 100 is easily inserted from the nasal cavity, and it is easily accessible and removable after its task has been completed.

Thus, the insert 100 and procedure for improving drainage in accordance with the invention offer significant advantages over conventional devices and procedures.

While the present invention is described with reference to specific embodiments, it will be apparent to persons skilled in the art that many modifications and variations are possible. Accordingly, the present invention embraces all alternatives, modifications and variations that fall within the spirit and scope of the appended claims and all equivalents thereof.

I claim:

1. A transnasal lacrimal insert, comprising:

a L-shaped tubular member having a passage extending therethrough, said tubular member having a proximal end and an enlarged distal end, said passage having a first portion having a first axis disposed between said proximal end and said distal end and a second portion having a second axis disposed between said distal end and said first portion, said second axis substantially perpendicular to said first axis; and an attachment element having a longitudinal axis disposed within said passage at said distal end of said tubular member about which ends of a tube can be fastened, said attachment element defining a first semi-circular aperture and a second semi-circular aperture, said first and said second semi-circular apertures in fluid communication with said passage, said longitudinal axis of said attachment element disposed substantially perpendicular to said first axis of said first portion of said L-shaped tubular member, wherein said tubular member and said attachment element comprise biocompatible material.

* * * * *